(12) United States Patent
Wildeman et al.

(10) Patent No.: US 8,809,213 B2
(45) Date of Patent: Aug. 19, 2014

(54) APPLICATOR FOR SANITIZING AND/OR DISINFECTING SOLUTION

(75) Inventors: Martin Wildeman, Spartanburg, SC (US); David R. Harry, Jr., Oak Ridge, NC (US); Michelis Hardegree, Columbus, NC (US); Lori S. Sears, Taylors, SC (US)

(73) Assignee: Tietex International, Ltd, Spartanburg, SC (US)

( * ) Notice: Subject to any disclaimer, the term of this patent is extended or adjusted under 35 U.S.C. 154(b) by 95 days.

(21) Appl. No.: 13/372,904

(22) Filed: Feb. 14, 2012

(65) Prior Publication Data

US 2012/0207652 A1 Aug. 16, 2012

Related U.S. Application Data

(60) Provisional application No. 61/442,547, filed on Feb. 14, 2011.

(51) Int. Cl.
*D04H 3/005* (2012.01)

(52) U.S. Cl.
USPC .......... 442/351; 442/334; 442/340; 442/344; 442/381; 442/382; 442/392; 442/401

(58) Field of Classification Search
CPC ....... D04H 3/005; D04H 3/011; D04H 3/016; D04H 3/018; D04H 3/08; D04H 3/10; D04H 3/115
USPC .......... 442/334, 340, 344, 351, 381, 392, 401
See application file for complete search history.

(56) References Cited

U.S. PATENT DOCUMENTS

| | | | |
|---|---|---|---|
| 5,487,936 A | * | 1/1996 | Collier .................... 442/214 |
| 6,427,493 B1 | * | 8/2002 | Kasdan et al. .......... 66/169 R |
| 6,667,290 B2 | | 12/2003 | Svendsen |
| 6,794,352 B2 | | 9/2004 | Svendsen |
| 6,916,776 B2 | | 7/2005 | Svendsen |
| 7,279,452 B2 | | 10/2007 | Svendsen et al. |
| 7,799,751 B2 | | 9/2010 | Kilkenny et al. |
| 2002/0189040 A1 | | 12/2002 | Svendsen |
| 2005/0245151 A1 | | 11/2005 | Annis |
| 2006/0135012 A1 | | 6/2006 | Laker |
| 2007/0142261 A1 | | 6/2007 | Clark et al. |
| 2011/0272304 A1 | | 11/2011 | Wahal et al. |

OTHER PUBLICATIONS

International Search Report and Written Opinion—PCT/US2013/026110.

* cited by examiner

*Primary Examiner* — Andrew Piziali
(74) *Attorney, Agent, or Firm* — J.M. Robertson, LLC

(57) ABSTRACT

A textile applicator for application of a sanitizing and/or disinfecting solution to a surface. The applicator incorporates a plurality of direct spun polyester microfiber yarns to define a textile surface which does not bind or inactivate quaternary ammonium compounds, chlorine-based or peracetic and/or other peroxygen based sanitizing and/or disinfecting agents. Thus, the sanitizing and/or disinfecting agent is readily released to the surface being treated without any requirement of pre-loading surface binding sites or applying a charge-modifying surface treatment.

18 Claims, 2 Drawing Sheets

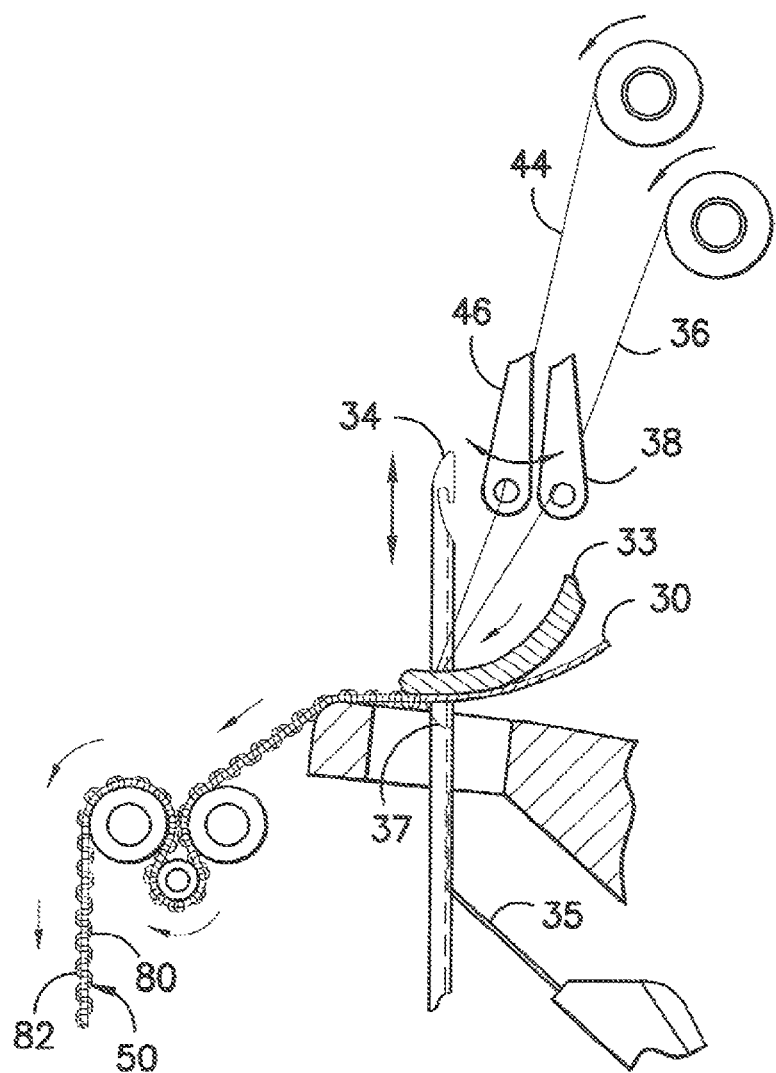
FIG. -1-

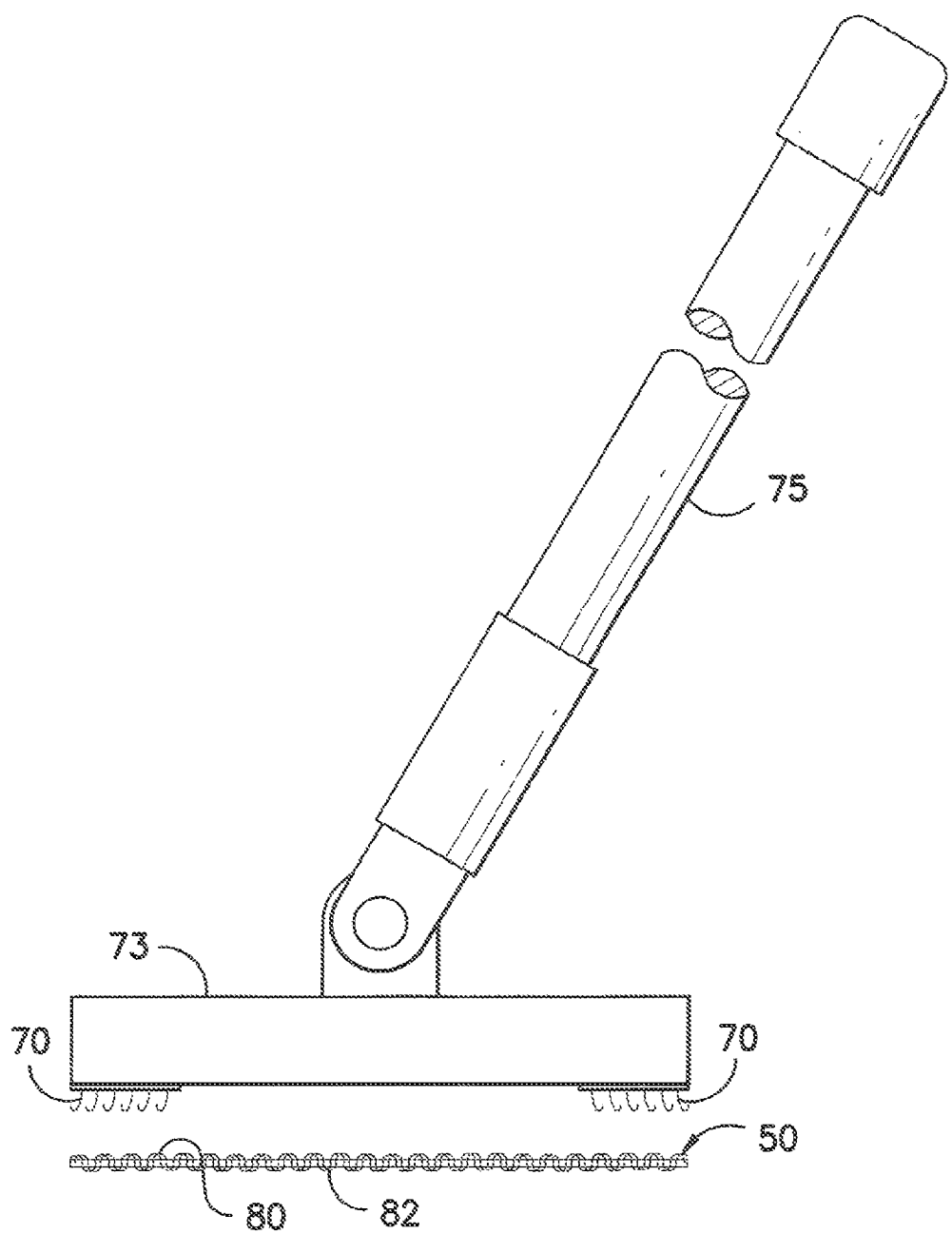
FIG. -2-

APPLICATOR FOR SANITIZING AND/OR DISINFECTING SOLUTION

CROSS REFERENCE TO RELATED APPLICATION

This nonprovisional application claims the benefit of, and priority from, U.S. provisional application 61/442,547 having a filing date of Feb. 14, 2011. The contents of such earlier application are hereby incorporated by reference in their entirety as if fully set forth herein.

TECHNICAL FIELD

The present invention relates generally to cleaning supplies, and more particularly, to applicators used in the dispersion of sanitizing and/or disinfecting solutions including but not limited to quaternary ammonium compounds or chlorine-based, and/or peracetic/peroxygen antimicrobial compositions while maintaining the concentration level of the sanitizing and/or disinfecting solution at an effective concentration level for use in treatment of surfaces in environments such as hospitals, restaurants, schools and the like. Such applicators may be in the form of hand-held wipes, floor mop covers or other suitable structures.

BACKGROUND OF THE INVENTION

It is well known to use polyester textile applicators to disperse cleaning and sanitizing and/or disinfecting solutions across surfaces to be treated. Such applicators may be formed from PET or other polyester polymer and have woven, knit, or non-woven constructions which act to carry a volume of the cleaning and sanitizing and/or disinfecting solution for subsequent discharge across the surface to be cleaned. Past applicators have also incorporated various textured surfaces to facilitate cleaning.

Many sanitizing and/or disinfecting solutions utilize an aqueous solution with an active sanitizing and/or disinfecting agent based on quaternary ammonium compounds (QUATS or QAC's) such as quaternary ammonium chloride or bromide surfactants and the like. Other solutions use chlorine, peracids and/or peroxides. QUATS are generally cationic in character and readily bind to most textile applicators which typically utilize anionic surfactant surface treatments. Such sanitizing and/or disinfecting agents may also bind to textile applicators free of anionic surfactant surface treatments with such binding typically being facilitated in the presence of an enhanced number of physical binding sites. Chlorine (hypochlorite) and peroxide based agents are oxidizers and are easily inactivated by substrates with reactive organic compositions such as cotton, cellulosic pulp or traditional microfiber structures.

Structurally, QUATS contain four carbon atoms, linked directly to one nitrogen atom through covalent bonds and four alkyl groups. The portion attached to the nitrogen atom may be any anion, but is usually chloride or bromide to form the salt. The nitrogen atom with the attached alkyl groups forms the positively charged cation portion. Depending on the nature of the R groups, the anion and the number of quaternary nitrogen atoms present, the compound may be classified as monoalkyltrimethyl, monoalkyldimethylbenzyl, heteroaromatic, polysubstituted quaternary, bis-quaternary, or polymeric quaternary ammonium compounds.

The binding and/or inactivation of QUAT, chlorine-based, peracetic and peroxygen sanitizing and/or disinfecting agents by textile applicators is a well known phenomenon and is generally understood to be undesirable. Specifically, binding the sanitizing and/or disinfecting agents to the applicators prevents their subsequent release for dispersion and surface treatment. Thus, the solution which is dispersed to the surface being treated may have much lower concentration of active sanitizing and/or disinfecting agent than anticipated. If concentrations of the active sanitizing and/or disinfecting agent are not maintained at effective levels, the reduction of microbial contaminants to safe levels may not be achieved on the surface being treated. As will be appreciated by those of skill in the art, for individual products, recommended concentrations for active sanitizing and/or disinfecting agents to achieve safe levels of microbial contaminant reduction may be set from time to time by controlling governmental agencies.

In the past, several approaches have been utilized to promote release of effective concentrations of sanitizing and/or disinfecting agents from textile applicators. A common approach has been to substantially saturate the applicator with sanitizing and/or disinfecting agent by immersing the applicator in a bucket containing an aqueous solution of the sanitizing and/or disinfecting agent until binding or oxidation is substantially completed with all available sites on the applicator. Once binding or oxidation is completed, the solution container is then emptied and an additional volume of the sanitizing and/or disinfecting agent is added to the solution in the bucket to bring the concentration of the sanitizing and/or disinfecting agent in the bucket fluid back up to the desired effective level. Thus, the fluid which is ultimately expelled from the applicator will have an adequate concentration of sanitizing and/or disinfecting agent. While this approach is effective, it is labor intensive and requires training. It also has the deficiency of requiring an enhanced volume of the sanitizing and/or disinfecting agent for use in reviving the concentration in the bucket.

Another approach has been to spray the disinfecting solution directly onto the surface being cleaned this approach has the advantage of avoiding absorption by the applicator. However, it may be difficult to achieve coverage of the underside of various structures. Also, spraying may result in users breathing in a portion of the applied disinfectant.

Another approach has been to treat the textile applicator with a cationic surfactant or other surface modification which does not attract and/or inactivate the cationic QUAT, chlorine, peracetic or peroxygen-based sanitizing and/or disinfecting agents. By way of example only, and not limitation, such an approach is described in U.S. Pat. No. 6,794,352 to Svendsen; U.S. Pat. No. 6,916,776 to Svendsen; and U.S. Reissue Pat. RE40,495 to Svendsen, the teaching of all of which are incorporated by reference as if fully set forth herein. While this approach may be effective, it requires the use of a surface treatment which may add cost and/or change the desired surface character of the applicator. Moreover, as best understood, there is an absence of a singular surface treatment which prevents attraction of QUATS while also avoiding activation of chlorine and other oxidizers. Thus, different products are marketed for different uses.

In the prior approaches described, the goal has been to reduce the number of active binding sites by either pre-loading those sites or by changing the ionic character at those sites such that they are inactive. Thus, it has been considered generally desirable to minimize the number of physical binding sites at the textile surface since a larger number of physical binding sites may provide a greater propensity for interaction and possible binding. In light of this desire to minimize the number of physical binding sites, the use of base textiles incorporating so called "microfibers" in combination with QUAT, chlorine-based or peracetic peroxygen sanitizing and/ or disinfecting agents has been avoided. In this regard, it has generally been believed that such microfiber textiles provide an excessive number of binding sites and will therefore bind or inactivate available sanitizing and/or disinfecting agents to an unsatisfactory degree.

In instances where pre-treated microfiber textiles have been used, it has generally been considered desirable to use so called conjugated "split" microfibers formed by a technique in which a large fiber is formed and then split into a plurality of smaller fibers with angled perimeters. Such angled perimeters have been believed to aid in scrubbing ultra fine particles to physically remove harmful bacteria which may grow on surfaces in hospitals, restaurants and similar environments.

In light of the above deficiencies in the known art there is a continuing need for a textile applicator which may incorporate the enhanced cleaning benefit of microfibers without binding or inactivating sanitizing and/or disinfecting agents, including but not limited to, QUATs, chlorine-based and other oxidizing agents and the like and without requiring a cationic or other surface modifying surfactant treatment.

SUMMARY OF THE INVENTION

The present invention provides advantages and alternatives over the prior art by providing a textile applicator of incorporating a plurality of direct spun polyester microfiber yarns. The applicator may be of warp knit, circular knit, woven, stitch-bonded or other construction as may be desired. In one exemplary embodiment a stitch-bonded construction is provided incorporating a plurality of direct spun textured polyester microfiber yarns stitched through a substrate material to define a textile surface which does not bind or inactivate QUATs, chlorine-based or peracetic and/or other peroxygen based sanitizing and/or disinfecting agents. Thus, the sanitizing and/or disinfecting agent is readily released to the surface being treated without any requirement of pre-loading surface binding sites or applying a charge-modifying surface treatment. Other exemplary aspects of the invention will become apparent upon review of the following detailed description of preferred embodiments and practices.

In accordance with one exemplary aspect, the present invention provides a textile applicator of fibrous construction for application of a liquid sanitizing or disinfecting solution to a surface. The applicator includes a plurality of multi-filament microfiber yarns in a stitch-bonded, knit or woven fabric construction forming a liquid carrier fabric for collection and dispersal of the sanitizing or disinfecting solution. The microfiber yarns comprise a plurality of direct spun polyester filaments characterized by a substantially circular cross sectional perimeter and a linear density of less than 1 denier per filament. The liquid carrier fabric is substantially free of any conjugated split fibers and substantially free of any amide-containing constituents. The liquid carrier fabric is nonreactive with both quaternary ammonium compounds and chlorine such that the concentration of quaternary ammonium compounds or chlorine in the sanitizing or disinfecting solution degrades by not more than about 10% following immersion of the liquid carrier fabric in the sanitizing or disinfecting solution for a period of one hour.

BRIEF DESCRIPTION OF THE DRAWINGS

The accompanying drawings, which are incorporated in, and which constitute a part of this specification, illustrate exemplary constructions and procedures in accordance with the present invention and, together with the general description of the invention given above and the detailed description set forth below, serve to explain the principles of the invention wherein:

FIG. 1 is a schematic view illustrating formation if an exemplary applicator material in accordance with the present invention; and FIG. 2 is a schematic view illustrating attachment of an applicator in accordance with the present invention to a user manipulated mop head.

While the invention has been illustrated and generally described above and will hereinafter be described in connection with certain potentially preferred embodiments and practices, it is to be understood that in no event is the invention limited to such illustrated and described embodiments and practices. On the contrary, it is intended that the present invention shall extend to all alternatives and modifications as may embrace the general principles of this invention within the full and true spirit and scope thereof.

DESCRIPTION OF THE PREFERRED EMBODIMENT(S)

Reference will now be made to the drawings, wherein to the extent possible like reference numerals are utilized to designate corresponding components throughout the various views. In FIG. 1 there is illustrated an exemplary stitch-bonding practice for use in forming an applicator in accordance with one exemplary embodiment of the present invention. By way of example only and not limitation stitch-bonding practices are illustrated and described in U.S. Pat. No. 8,060,973 to Wildeman et al., the contents of which are hereby incorporated by reference in their entirety. In the illustrated exemplary practice, one or more plies of a stitching substrate material 30 of fibrous nonwoven construction such as a spun bonded fleece, or carded thermobond web of polypropylene may be conveyed to a stitch-forming position in the direction indicated by the arrows. In the event that multiple plies of substrate material 30 are used, such multiple plies cooperatively form the substrate structure. The total mass per unit area of the substrate structure is preferably in the range of about 15 to 150 grams per square meter, and is preferably about 40 grams per square meter, although higher or lower weights may be used if desired.

In accordance with one potentially desirable construction, the substrate material may be one or more layers of spun-bonded polypropylene fleece. However, other polypropylene materials may also be used. It s also contemplated that polyester such as PET (polyethylene terephthalate) or other polyester may be used if desired. The substrate material 30 may be delivered without significant underfeed or overfeed. However, delivery rates may be adjusted as desired. By way of example only, in one exemplary construction two layers of substrate material 30 in the form of spunbonded polypropylene or polyester fleece with each having a mass per unit area of about 15 grams per square meter may be delivered to the stitching position in an overfeed condition to provide a consolidation during stitching of about 1.35 such that the final stitched substrate has a mass per unit area of about 40.5 grams per square meter.

As illustrated, the stitch bonding machine typically incorporates a row of reciprocating needles 34 (only one shown) extending in adjacent relation to one another across the width of the substrate material 30 substantially transverse to the direction of movement of the substrate material 30. So called "sinker fingers" 33 (also known as nebs) may extend from a sinker bar for disposition between the needles to aid in pressing the plies of substrate material together and to hold segments of stitching yarns which cross between needles in slightly raised relation from the substrate material 30. In one practice, the sinker fingers 33 may be set at about 2.1 mm forward to form loops on both sides of the formed fabric. The sinker fingers 33 may also be eliminated if desired. By way of example only, and not limitation, the sinker fingers 33 may have a height of about 0.5 mm to 4 mm and most preferably about 2 mm although other sizes may likewise be used.

According to the illustrated exemplary practice, two yarn systems (i.e. two bars) are used to form stitches through the substrate material 30. A first group of so called microfiber yarns 36 is carried by a first guide 38 for fully threaded engagement with the needles 34. In this regard, it is to be understood that the term "microfiber yarn" denotes a multi-filament yarn formed from a plurality of filaments (i.e. elongate fibers) characterized by a linear density of less than 1 denier per filament (dpf). More preferably, such microfiber yarns 36 are formed predominantly on a weight basis from fibers characterized by a linear density in the range of about 0.3 to about 0.7 dpf. By way of example only, and not limitation, one exemplary microfiber yarn 36 is a 150 denier/288 filament textured yarn formed from direct spun polyester (PET) fibers having a denier per filament rating of about 0.52 dpf. Another exemplary microfiber yarn 36 is a 150 denier/408 filament textured yarn formed from direct spun polyester (PET) fibers having a denier per filament rating of about 0.36 dpf. Of course, higher or lower denier levels may be used if desired. As will be appreciated, the direct spun fibers are characterized by a substantially cylindrical construction with a circular cross-section.

In the illustrated exemplary construction, a second group of standard denier yarns 44 may be carried by a second guide 46 for fully threaded engagement with the needles 34. By way of example only, and not limitation, one exemplary standard denier multi-filament yarn is a 40/12 semi-dull, round fully oriented polyester although other yarns also may be used. The standard denier yarns 44 provide structural integrity but may be eliminated if desired such that all yarns are microfiber yarn.

As will be appreciated by those of skill in the art, during the stitch-bonding process a needle 34 (shown in greatly exaggerated dimension) pierces the substrate material 30 and engages stitching yarns delivered into position by the yarn guides such that the stitching yarns are captured within a hook portion of the needle 34. As the needle is reciprocated downwardly, a closing element 35 such as a closing wire which moves relative to the needle 34 closes the hook portion to hold the stitching yarns therein. With the hook portion closed, the captured stitching yarns are pulled through the interior of an immediately preceding yarn loop 37 disposed around the shank of the needle 34 at a position below the substrate material 30. As the captured stitching yarns are pulled through the interior of the preceding yarn loop 37 a stitch is formed which is knocked off of the needle 34. As the needle 34 is raised back through the substrate material 30, the hook portion is reopened and a new yarn loop 37 moves out of the hook portion and is held around the shank of the needle 34 for acceptance of captured yarns and formation of a subsequent stitch during the next down stroke. During this process individual stitching yarns may be held at a single needle 34 or may be shifted back and forth laterally between needles between stitches. As will be appreciated, outwardly projecting loops may be formed across the upper surface by passing the stitching yarns back and forth between needles with sinker fingers disposed between the needles. In some instances, the presence of such loops may aid in cleaning.

The so called gauge or needle density in the cross machine direction maybe adjusted as desired. By way of example only, and not limitation, it is contemplated that the gauge may be in the range of about 7 to 28 needles per inch and will more preferably be about 12 to 16 and will most preferably be about 14 needles per inch, although higher and lower needle densities may likewise be used if desired. By way of example only, and not limitation, the stitch bonding machine may be set to apply stitches in the machine direction at a level of about 4 to about 25 stitches per inch (also referred to as courses per inch or CPI) and will more preferably apply stitches in the machine direction at a level of about 8 to about 20 CPI and will most preferably apply stitches in the machine direction at a level of about 14 to about 18 CPI although higher and lower stitch densities may likewise be used if desired.

According to one exemplary practice, the microfiber yarns 36 may be stitched in a tricot pattern according to the stitch notation (1-0, 1-2)// while the standard denier yarns 44 may be stitched in a chain stitch pattern according to the stitch notation (1-0, 0-1)//. Thus, the microfiber yarns 36 extend in a zigzag pattern while the standard denier yarns 44 extend in straight parallel rows. According to another exemplary practice, the microfiber yarn 36 may be stitched according to the stitch notation (1-0, 1-2, 2-3, 3-4, 4-5, 5-6, 6-7, 7-8, 8-9, 8-7, 7-6, 6-5, 5-4, 4-3, 3-2, 2-1)// while the standard denier yarns 44 may be stitched in a chain stitch pattern according to the stitch notation (1-0, 0-1)//. Thus, the microfiber yarns 36 form a large chevron pattern while the standard denier yarns 44 extend in straight parallel rows. Of course, other stitch notations may likewise be used.

As will be appreciated, the resultant stitch-bonded fabric construction 50 may be segmented into desired geometries for use as hand-held wipes or for attachment to a mop head. The fabric construction 50 thus defines a liquid carrier fabric for collection and dispersal of a sanitizing or disinfecting solution, In this regard, it will be understood that the use of the microfiber stitching yarn may provide a further advantage by presenting a large surface area of fine fibers across the so called "technical face" corresponding to the underside in FIG. 1 which may act to grip hooking elements on the face of the mop head to form a hook and loop connection system.

While an applicator of stitch-bonded construction may be desirable in many environments of use, it is likewise contemplated that other fabric constructions incorporating direct spun polyester microfiber yarns may also be used. By way of example only, and not limitation, other fabric constructions may include nonwovens, warp knit, circular knit and woven constructions as may be desired.

By way of example only, and not limitation, FIG. 2 illustrates an exemplary mop having a mop head 73 connected to an elongated handle 75. Hooking elements 70 project away from a lower surface of the mop head. In practice, the microfiber stitching yarns define a high surface area connection surface 80 across the technical face of the fabric construction 50 where the stitches are locked with a cleaning surface 82 of loops across the technical back. This construction permits the establishment of a peel-away bond to the hooking elements 70 during use.

A significant feature of the present invention is the use of direct spun microfibers of circular cross-section rather than the more common conjugated split fibers which are characterized by angular perimeter surfaces. In this regard, the use of such direct spun microfibers with round perimeters has surprisingly been found to provide excellent scrubbing bacteria removal while also reducing the propensity for QUAT and chlorine binding and/or inactivation. Conversely, split fibers of similar dpf levels greatly enhance QUAT and chlorine binding or inactivation.

EXAMPLES

The invention may be further understood through reference to the following non-limiting examples.

Examples 1-2

One hundred gram samples of two-bar stitch-bonded wipe material were tested for binding of Quaternary Ammonium compound agent in aqueous solution. Each of the samples incorporated a 40 gram per square meter polypropylene spun-bonded substrate with one bar of 63/40/12 semi-dull round polyester stitched in a (1-0,0-1)// stitch notation. The sample of Example 1 incorporated a bar of 150 denier/288 filament textured polyester yarn formed from direct spun microfibers stitched in a (1-0, 1-2)// stitch notation. No ionic surfactant treatment was applied. The sample of Example 2 incorporated a bar of 150 denier/408 filament textured polyester yarn formed from direct spun microfibers stitched in a (1-0, 1-2)// stitch notation. No ionic surfactant treatment was applied.

Test Procedure:
1) Bulk Quaternary Solution Feedstock for Test
   a) 15 grams of a 23% Quaternary Ammonium was diluted in approximately five gallons of water
   b) 5 grams of the solution was added to the test tube instead of using visual measurements
   c) Feedstock solution was determined to be approximated 400 ppm based on a commercial LaMotte QUAT Test Kit, Model QAC, Code 7057.
2) Approximately 1400 ml of stock solution was added to containers for the wipes
3) The wipes were placed into individual containers containing the QUAT solutions
4) Each QUAT solution was measured after one hour using the test kit to determine if there was any immediate reduction of quaternary activity.
5) The measurements were repeated for each solution at 1-hour, 19-hours, 24-hours and 48 hours of contact time.

Results:

| Quaternary Solution - 400 ppm | 1-hour | 19-hours | 24-hours | 48-hours |
| --- | --- | --- | --- | --- |
| 150/288 wipe | 390 ppm | 380 ppm | 380 ppm | 380 ppm |
| 150/408 wipe | 390 ppm | 390 ppm | 380 ppm | 390 ppm |

Despite the absence of ionic adjustment, there was no obvious or loss of quaternary activity in the test solution thereby indicating an absence of significant bonding to the wipes. The LaMotte test kit is quantitative but limited in accuracy due to the small sample size of 5 ml equated to 10 ppm for each drop from the dropper bottle during titration and color interpretation will allow for a variance of, plus or minus 20 ppm depending on operator and endpoint interpretation.

Typical textile materials display substantial interaction within one hour and continued exhibiting degradation with time.

Examples 3-4

One hundred gram samples of two-bar stitch-bonded wipe material were tested for binding of Quaternary Ammonium compound sanitizing agent in aqueous solution. Each of the samples incorporated a 40 gram per square meter polypropylene spun-bonded substrate with one bar of 63/40/12 semi-dull round polyester stitched in a (1-0,0-1)// stitch notation. The sample of Example 1 incorporated a bar of 150 denier/288 filament textured polyester yarn formed from direct spun microfibers stitched in a (1-0, 1-2)// stitch notation. No ionic surfactant treatment was applied. The sample of Example 2 incorporated a bar of 150 denier/408 filament textured polyester yarn formed from direct spun microfibers stitched in a (1-0, 1-2)// stitch notation. No ionic surfactant treatment was applied.

Test Procedure:
1. 14.02 grams of a 5.75% Clorox® solution was diluted in 8 liters of water.
2. The solution was titrated and confirmed to be 100 ppm chlorine using a HACH Total Chlorine Test Kit, 10-200 mg/L Model CN-21P.
3. 1000 ml of stock solution was added to 8 containers.
4. The wipes were placed into the individual containers containing the chlorine solutions.
5. Chlorine concentrations were measured immediately and at 1 hour intervals following the addition of the selected materials up to 4 hours and also at 48 hours.

Results:

| 100 ppm Bleach Solution | Immediate | 1-hour | 2-hours | 3-hours | 4-hours | 48-hours |
| --- | --- | --- | --- | --- | --- | --- |
| Wipes—150/288, 100 grams | 100 ppm | 100 ppm | 100 ppm | 100 ppm | 100 ppm | 60 ppm |
| Wipes—150/408, 100 grams | 100 ppm | 100 ppm | 100 ppm | 100 ppm | 100 ppm | 60 ppm |

There was no obvious or loss off chlorine activity for the wipes tested and fibers recorded in Table 1 based on the limitations of the HACH chlorine test kit; which is quantitative but limited in accuracy to 10 ppm.

Bacterial Removal:

Applicators incorporating direct spun microfibers according to the present invention have been shown to provide bacterial removal performance which is equivalent or better than commercial products formed from conjugated split microfibers and wipes is QUAT resistant surfactant surface treatments. Such bacterial removal performance is set forth in the following table.

| Bacterial Removal Tests | | | |
| --- | --- | --- | --- |
| Wipes | e-coli on stainless | MRSA on stainless | MRSA on pourous vinyl |
| 150/408 full-thread microfiber - sanitizer and disinfectant resistant | 99.6814 | 93.2518 | 89.7132 |
| 150/288 full-thread microfiber sanitizer and disinfectant resistant | 97.6018 | 94.429 | not tested |
| little chevron wipe - 50% 150/408 | 92.7256 | 94.5463 | not tested |
| Woven commercial microfiber hand cloth - not sanitizer or disinfectant resistant | 93.6904 | 92.1786 | not tested |
| Non-woven commercial wipe - that is quat resistant only | 95.6116 | 95.8553 | not tested |

Testing error is + or −0.5%

Comparative Examples 1-8

QUAT. Resistance Relative to other Microfiber Products

The testing procedures of Examples 1 and 2 were carried out on a 100 gram sample of two-bar stitch bonded wipe incorporating exemplary multifilament stitching yarns of direct spun microfiber filaments stitched through a polypropylene substrate such that the stitching yarns consisted essentially of PET microfiber with substantially round filaments and with no amide constituent. The same testing procedures were applied to 100 gram samples of various microfiber products purchased from retail establishments. The direct spun microfiber samples incorporated two layers of substrate material in the form of spunbonded polypropylene fleece with each having a mass per unit area of about 15 grams per square meter with a consolidation during stitching of about 1.35 such that the final stitched substrate has a mass per unit area of about 40.5 grams per square meter. One bar was fully threaded with 40/12 semi-dull round polyester stitched in a (1-0,0-1)// stitch notation. The second bar was fully threaded with 150 denier/288 filament textured polyester yarn formed from direct spun microfibers stitched in a (1-0, 1-2, 2-3, 3-4, 4-5, 5-6, 6-7, 7-8, 8-9, 8-7, 7-6, 6-5, 5-4, 4-3, 3-2, 2-1)// stitch notation to yield a large chevron pattern. No ionic surfactant treatment was applied.

| Material | Polyester/Amide | 1 hour | 2 hours | 3 hours | 4 hours | 8 hours | 24 hours |
|---|---|---|---|---|---|---|---|
| 150/288 wipe | PET Stitch Bonded Through Polypropylene Substrate (No Amide) | 400 ppm | 400 ppm | 400 ppm | 400 ppm | 400 ppm | 380 ppm |
| Retail Purchased Multifunction Microfiber Wipe | 85/15 | 260 | 250 | 230 | 220 | 210 | 180 |
| Retail Purchased Dusting Microfiber Wipe | 87/13 | 310 | 260 | 250 | 250 | 240 | 230 |
| Retail Purchased Kitchen Microfiber Wipe | 90/10 | 350 | 330 | 310 | 310 | 300 | 270 |
| Retail Purchased Microfiber Towel | 80/20 | 320 | 300 | 290 | 280 | 270 | 230 |
| Retail Purchased Bar Cloth | 100/0 | 350 | 340 | 330 | 320 | 310 | 290 |
| Retail Purchased Bed Sheet (Washed) | 100/0 | 360 | 350 | 340 | 330 | 330 | 300 |
| Retail Purchased Bed Sheet (Unwashed) | 100/0 | 360 | 350 | 340 | 330 | 330 | 300 |

Testing error is + or −0.5%

Comparative Examples 9-16

Chlorine Resistance Relative to other Microfiber Products

The testing procedures of Examples 3 and 4 were carried out on a 100 gram sample of a two-bar stitch bonded wipe material incorporating exemplary multifilament stitching yarns of direct spun microfiber filaments stitched through a polypropylene substrate as described in Comparative Examples 1-8 such that the stitching yarns consisted essentially of PET microfiber with substantially round filaments and with no amide constituent. The same testing procedures were applied to 100 gram samples of microfiber products purchased from various retail establishments.

| Material | Polyester/Amide | 1 hour | 2 hours | 3 hours | 4 hours | 8 hours | 24 hours |
|---|---|---|---|---|---|---|---|
| 150/288 wipe | PET Stitch Bonded Through Polypropylene Substrate (No Amide) | 100 ppm | 100 ppm | 100 ppm | 100 ppm | 90 ppm | 80 ppm |
| Retail Purchased Multifunction Microfiber Wipe | 85/15 | 80 | 70 | 70 | 60 | 50 | 10 |

-continued

| Material | Polyester/Amide | 1 hour | 2 hours | 3 hours | 4 hours | 8 hours | 24 hours |
|---|---|---|---|---|---|---|---|
| Retail Purchased Dusting Microfiber Wipe | 87/13 | 80 | 70 | 70 | 60 | 50 | 50 |
| Retail Purchased Kitchen Microfiber Wipe | 90/10 | 80 | 70 | 70 | 70 | 60 | 40 |
| Retail Purchased Microfiber Towel | 80/20 | 80 | 70 | 70 | 70 | 70 | 60 |
| Retail Purchased Bar Cloth | 100/0 | 80 | 70 | 70 | 70 | 70 | 50 |
| Retail Purchased Bed Sheet (Washed) | 100/0 | 80 | 80 | 80 | 80 | 80 | 70 |
| Retail Purchased Bed Sheet (Unwashed) | 100/0 | 80 | 80 | 80 | 80 | 80 | 70 |

Testing error is + or −10 ppm

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A textile applicator of fibrous construction for application of a liquid sanitizing or disinfecting solution to a surface, the applicator comprising:

a plurality of multi-filament microfiber yarns in a stitch-bonded fabric construction forming a liquid carrier fabric for collection and dispersal of the sanitizing or disinfecting solution, wherein the microfiber yarns comprise a plurality of direct spun polyester filaments characterized by a substantially circular cross sectional perimeter and a linear density of less than 1 denier per filament and wherein the liquid carrier fabric is substantially free of any conjugated split fibers and substantially free of any amide-containing constituent, the liquid carrier fabric being nonreactive with both quaternary ammonium compounds, and chlorine such that the concentration of quaternary ammonium compounds or chlorine in the sanitizing or disinfecting solution degrades by not more than about 10% following immersion of the liquid carrier fabric in the sanitizing or disinfecting solution for a period of one hour, and wherein the microfiber yarns are stitched through at least one layer of polypropylene or polyester fleece.

2. The textile applicator as recited in claim 1, wherein the liquid carrier fabric is a stitch bonded fabric comprising the microfiber yarns stitched through a plurality of layers of polypropylene or polyester fleece.

3. The textile applicator as recited in claim 1, wherein the liquid carrier fabric is a stitch bonded fabric comprising the microfiber yarns stitched through at least one layer of spunbonded polypropylene fleece in combination with a plurality of standard denier multi-filament polyester yarns stitched through said at least one layer of spunbonded polypropylene fleece.

4. The textile applicator as recited in claim 3, wherein the liquid carrier fabric is a stitch bonded fabric comprising the microfiber yarns stitched through a plurality of layers of spunbonded polypropylene fleece in combination with a plurality of standard denier multi-filament polyester yarns stitched through said plurality of layers of spunbonded polypropylene fleece.

5. The textile applicator as recited in claim 1, wherein the microfiber yarns consist essentially of a plurality of direct spun polyester filaments characterized by a substantially circular cross sectional perimeter and a linear density of in the range of about 0.3 to about 0.7 denier per filament.

6. The textile applicator as recited in claim 1, wherein the microfiber yarns consist essentially of a plurality of direct spun polyester filaments characterized by a substantially circular cross sectional perimeter and a linear density of in the range of about 0.3 to about 0.5 denier per filament.

7. The textile applicator as recited in claim 1, wherein the polypropylene stitching substrate comprises a plurality of layers of polypropylene fleece.

8. A textile applicator of fibrous construction for application of a liquid sanitizing or disinfecting solution to a surface, the applicator comprising:
a plurality of multi-filament microfiber yarns in a stitch-bonded, fabric construction forming a liquid carrier fabric for collection and dispersal of the sanitizing or disinfecting solution, wherein the microfiber yarns consist essentially of a plurality of direct spun polyester filaments characterized by a substantially circular cross sectional perimeter and a linear density of in the range of about 0.3 to about 0.7 denier per filament and wherein the liquid carrier fabric is substantially free of any conjugated split fibers and substantially free of any amide-containing constituent, the liquid carrier fabric being nonreactive with both quaternary ammonium compounds, and chlorine such that the concentration of quaternary ammonium compounds or chlorine in the sanitizing or disinfecting solution degrades by not more than about 10% following immersion of the liquid carrier fabric in the sanitizing or disinfecting solution for a period of one hour, and wherein the liquid carrier fabric is a stitch bonded fabric comprising the microfiber yarns stitched through at least one layer of polypropylene stitching substrate.

9. The textile applicator as recited in claim 8, wherein the polypropylene stitching substrate comprises at least one layer of spunbonded polypropylene fleece.

10. The textile applicator as recited in claim 8, wherein the liquid carrier fabric is a stitch bonded fabric comprising the microfiber yarns stitched through at least one layer of spunbonded polypropylene fleece in combination with a plurality of standard denier multi-filament polyester yarns stitched through said at least one layer of spunbonded polypropylene fleece.

11. The textile applicator as recited in claim 10, wherein the liquid carrier fabric is a stitch bonded fabric comprising the microfiber yarns stitched through a plurality of layers of spunbonded polypropylene fleece in combination with a plurality of standard denier multi-filament polyester yarns stitched through said plurality of layers of spunbonded polypropylene fleece.

12. The textile applicator as recited in claim 8, wherein the microfiber yarns consist essentially of a plurality of direct spun polyester filaments characterized by a substantially circular cross sectional perimeter and a linear density of in the range of about 0.3 to about 0.5 denier per filament.

13. A textile applicator of fibrous construction for application of a liquid sanitizing or disinfecting solution to a surface, the applicator comprising:
a plurality of multi-filament microfiber yarns in a stitch-bonded fabric construction forming a liquid earner fabric for collection and dispersal of the sanitizing or disinfecting solution, wherein the microfiber yarns consist of a plurality of direct spun polyester filaments characterized by a substantially circular cross sectional perimeter and a linear density of in the range of about 0.3 to about 0.7 denier per filament and wherein the liquid carrier fabric s substantially free of any conjugated split fibers and substantially free of any amide-containing constituent, the liquid carrier fabric being nonreactive with both quaternary ammonium compounds, and chlorine such that the concentration of quaternary ammonium compounds or chlorine in the sanitizing or disinfecting solution degrades by not more than about 10% following immersion of the liquid carrier fabric in the sanitizing or disinfecting solution for a period of one hour, and wherein the liquid carrier fabric is a stitch bonded fabric comprising the microfiber yarns stitched through at least one layer of polypropylene stitching substrate.

14. The textile applicator as recited in claim 13, wherein the polypropylene stitching substrate comprises at least one layer of spunbonded polypropylene fleece.

15. The textile applicator as recited in claim 13, wherein the polypropylene stitching substrate comprises a plurality of layers of polypropylene fleece.

16. The textile applicator as recited in claim 13, wherein the liquid carrier fabric is a stitch bonded fabric comprising the microfiber yarns stitched through at least one layer of spunbonded polypropylene fleece in combination with a plurality of standard denier multi-filament polyester yarns stitched through said at least one layer of spunbonded polypropylene fleece.

17. The textile applicator as recited in claim 16, wherein the liquid carrier fabric is a stitch bonded fabric comprising the microfiber yarns stitched through a plurality of layers of spunbonded polypropylene fleece in combination with a plurality of standard denier multi-filament polyester yarns stitched through said plurality of layers of spunbonded polypropylene fleece.

18. The textile applicator as recited in claim 17, wherein the microfiber yarns consist essentially of a plurality of direct spun polyester filaments characterized by a substantially circular cross sectional perimeter and a linear density of in the range of about 0.3 to about 0.5 denier per filament.

* * * * *